US00PP26359P2

(12) United States Plant Patent
Jandrew

(10) Patent No.: US PP26,359 P2
(45) Date of Patent: Jan. 26, 2016

(54) ***PENTAS* PLANT NAMED 'PEZZ0004'**

(50) Latin Name: *Pentas lanceolata*
Varietal Denomination: PEZZ0004

(71) Applicant: Syngenta Crop Protection AG, Basel (CH)

(72) Inventor: Jason Jandrew, Nipomo, CA (US)

(73) Assignee: Syngenta Crop Protection AG, Basel (CH)

( * ) Notice: Subject to any disclaimer, the term of this patent is extended or adjusted under 35 U.S.C. 154(b) by 130 days.

(21) Appl. No.: 13/998,411

(22) Filed: Oct. 30, 2013

Related U.S. Application Data

(60) Provisional application No. 61/891,955, filed on Oct. 17, 2013.

(51) Int. Cl.
*A01H 5/02* (2006.01)

(52) U.S. Cl.
USPC ..... Plt./466

(58) Field of Classification Search
USPC ..... Plt./466
See application file for complete search history.

*Primary Examiner* — Anne Grunberg
(74) *Attorney, Agent, or Firm* — Joshua L. Price

(57) ABSTRACT

A new *Pentas* plant named 'PEZZ0004' particularly distinguished by the large sized inflorescences with red colored flowers, dark yellow-green foliage, vigorous and upright habit with strong branches, and tolerates hot summer conditions.

1 Drawing Sheet

Latin name of the genus and species of the plant claimed: *Pentas lanceolata.*

Varietal denomination: 'PEZZ0004'.

BACKGROUND OF THE NEW PLANT

The present invention comprises a new *Pentas*, botanically known as *Pentas lanceolata,* and hereinafter referred to by the variety name 'PEZZ0004'.

'PEZZ0004' is a product of a planned breeding program. The new cultivar 'PEZZ0004' has large sized inflorescences with red colored flowers, dark yellow-green foliage, vigorous and upright habit with strong branches, and tolerates hot summer conditions.

'PEZZ0004'originates from a hybrid cross in a breeding program made in July 2006 in a greenhouse in Gilroy, Calif. The female parent was an unpatented, proprietary plant, identified as 'T50H-4' with violet colored flowers.

The male parent of 'PEZZ0004'was an unpatented, proprietary plant identified as 'T37H-1' with red colored flowers. The resultant seed was sown in January 2007 in a greenhouse in Gilroy, Calif.

'PEZZ0004' was selected as one flowering plant within the progeny of the stated cross in May 2007 in a greenhouse in Gilroy, Calif.

The first act of asexual reproduction of 'PEZZ0004' was accomplished when vegetative cuttings were propagated from the initial selection in May 2007 in a greenhouse in Gilroy, Calif.

BRIEF SUMMARY OF INVENTION

Horticultural examination of plants grown from cuttings of the plant initiated in May 2007 in Gilroy, Calif., and continuing thereafter, has demonstrated that the combination of characteristics as herein disclosed for 'PEZZ0004'are firmly fixed and are retained through successive generations of asexual reproduction.

'PEZZ0004' has not been observed under all possible environmental conditions. The phenotype may vary significantly with variations in environment such as temperature, light intensity, and day length.

A Plant Breeder's Right for this cultivar was applied for in Canada on Nov. 2, 2012, No. 12-7781 and was granted as certificate number 4942 on Oct. 29, 2014. 'PEZZ0004' has not been made publicly available more than one year prior to the filing of this application.

The following traits have been repeatedly observed and are determined to be basic characteristics of the new variety. The combination of these characteristics distinguishes this *Pentas* as a new and distinct variety.

BRIEF DESCRIPTION OF THE PHOTOGRAPHS

The accompanying photographic drawing shows typical flower and foliage characteristics of 'PEZZ0004' with colors being as true as possible with an illustration of this type.

The photographic drawing shows two flowering plants of the new variety growing in one container and a close-up of a flower.

DETAILED BOTANICAL DESCRIPTION

The plant descriptions, measurements and photographs were taken in Gilroy, Calif. in mid April 2013 under natural light. These plants were approximately 16-18 weeks old and were grown two plants per one gallon container in a greenhouse trial.

Color references are made to The Royal Horticultural Society Colour Chart (R.H.S.) 2001.

TABLE 1

DIFFERENCES BETWEEN THE NEW VARIETY 'PEZZ0004' AND A MOST SIMILAR VARIETY

| | 'PEZZ0004' | 'Bismarck Pink' (U.S. Plant Pat. No. 15,780) |
|---|---|---|
| Habit: | Much more vigorous | Less vigorous |
| Leaf size: | Larger | Smaller |
| Flower color/size: | Larger/red | Smaller/pink |

TABLE 2

DIFFERENCES BETWEEN THE NEW VARIETY 'PEZZ0004' AND MALE PARENT 'T37H-1'

| | 'PEZZ0004' | 'T37H-1' |
|---|---|---|
| Habit: | More rounded, less spreading | Less rounded, more spreading |

Plant:

*Form, growth and habit.*—Upright, sturdy and vigorous growth habit; good heat tolerance with continuous flowering through summer; well-branched plant habit.

*Plant height.*—21-23.0 cm.

*Plant height (inflorescence included).*—27-29.0 cm.

*Plant width.*—About 15.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Arrangement.*—Opposite.

*Immature leaf, color upper surface.*—Closest to RHS 147A; very glossy looking.

*Immature leaf, color lower surface.*—Closest to RHS 147B.

*Mature leaf, color upper surface.*—Closest to RHS 147A but slightly darker; much less glossy looking than immature.

*Mature leaf, color lower surface.*—Closest to RHS 147B.

*Length.*—7.5-8.2 cm.

*Width.*—4.4-4.7 cm.

*Shape.*—Broadly ovate to elliptical.

*Base shape.*—Attenuate.

*Apex shape.*—Acute.

*Margin.*—Entire.

*Texture upper side.*—Hirsute to slightly pilose.

*Texture lower side.*—Hirsute mainly along the veins.

*Color of veins, upper surface.*—RHS 144C.

*Color of veins, lower surface.*—RHS 144C.

*Pattern of veining.*—Pinnate.

*Petiole color.*—RHS 144C.

*Petiole length.*—0.5-0.7 cm.

*Diameter of petiole.*—0.3 cm.

*Texture.*—Hirsute to slightly pilose.

Stem:

*Quantity of branches.*—2-3.

*Color of stem.*—Closest to RHS 144A.

*Length of stem.*—19-24.0 cm.

*Diameter.*—0.3-0.4 cm.

*Length of internodes.*—4-7.0 cm.

*Texture.*—Hirsute to slightly pilose.

Peduncle:

*Color of peduncle.*—RHS 144A.

*Length of peduncle.*—1-1.4 cm.

*Peduncle diameter.*—0.3 cm.

*Peduncle texture.*—Hirsute to slightly pilose.

Pedicel:

*Color of pedicel.*—RHS 144A.

*Length of pedicel.*—0.2-0.3 cm.

*Diameter of pedicel.*—0.1 cm.

*Pedicel texture.*—Hirsute to slightly pilose.

Bud (just before opening):

*Color.*—RHS 185B.

*Length.*—2.4-2.6 cm.

*Width.*—0.4 cm.

*Shape.*—Oblong.

Inflorescence:

*Type.*—Terminal corymb; but more umbel looking.

*Natural flowering.*—Late spring and summer, flowers continuously.

*Number of inflorescences per plant.*—3-4 with open flowers; 2-3 immature with just buds.

*Fragrance.*—None.

*Inflorescence diameter.*—9-10.0 cm.

*Inflorescence depth.*—4.5-5.0 cm.

Corolla:

*Form.*—Single, tubular-shaped flowers consisting of a single whorl of 5 pointed petals fused at the base; aspect, flat; very free flowering.

*Lastingness of individual flowers.*—About 3-4 weeks depending on temperature.

*Diameter of floret.*—2.3-2.4 cm.

*Depth of floret.*—2.5-3.0 cm.

*Immature.*—Color upper petals, upper surface: RHS 53A but much brighter. Color upper petals, lower surface: Closest to RHS 55A.

*Mature.*—Color upper petals, upper surface: Between RHS 53A and RHS 53B. Color upper petals, lower surface: Closest to RHS 55B.

*Length petals.*—1.0 cm.

*Width of petals.*—0.5-0.55 cm.

*Petal shape.*—Ovate.

*Apex shape.*—Acute.

*Margin.*—Entire, where not fused.

*Base.*—Fused.

*Petal texture.*—Papillose; with some hairs down the midvein.

*Corolla tube color, inside.*—RHS N155B.

*Corolla tube color, outside.*—Closest to RHS 55B.

*Corolla tube length.*—2-2.1 cm.

*Corolla tube diameter.*—0.2 cm.

*Corolla throat diameter.*—0.5 cm.

Calyx:

*Number of sepals.*—5.

*Color of sepals.*—Closest RHS 147A.

*Length of sepals.*—0.8-0.9 cm.

*Width of sepals.*—0.15 cm.

*Sepal shape.*—Narrowly lanceolate.

*Apex shape.*—Acute.

*Margins.*—Entire.

*Texture, upper surface.*—Glabrous, with hairs at the margins.

*Texture, lower surface.*—Hirsute.

Reproductive organs:

*Gynoecium*.—Pistil: 1. Length: 2.8 cm. Style color: RHS 155C. Style length: 2.0 cm. Stigma color: Closest to RHS 59B but a little more grey. Sigma type: Bi-parted; pubescent. Ovary color: RHS N144A. Ovary length: 0.1 cm. Ovary diameter: 0.1 cm.

*Androecium*.—Number of stamens: 5. with filaments fused to the corolla wall. Anther color: RHS 197B. Length of anthers: 0.2 cm. Color of pollen: RHS 155A. Pollen amount: Normal.

Fertility/seed set: Has not been determined to date.

Disease/pest resistance: Has not been determined to date.

What is claimed is:

1. A new and distinct variety of *Pentas* plant named 'PEZZ0004' substantially as illustrated and described herein.

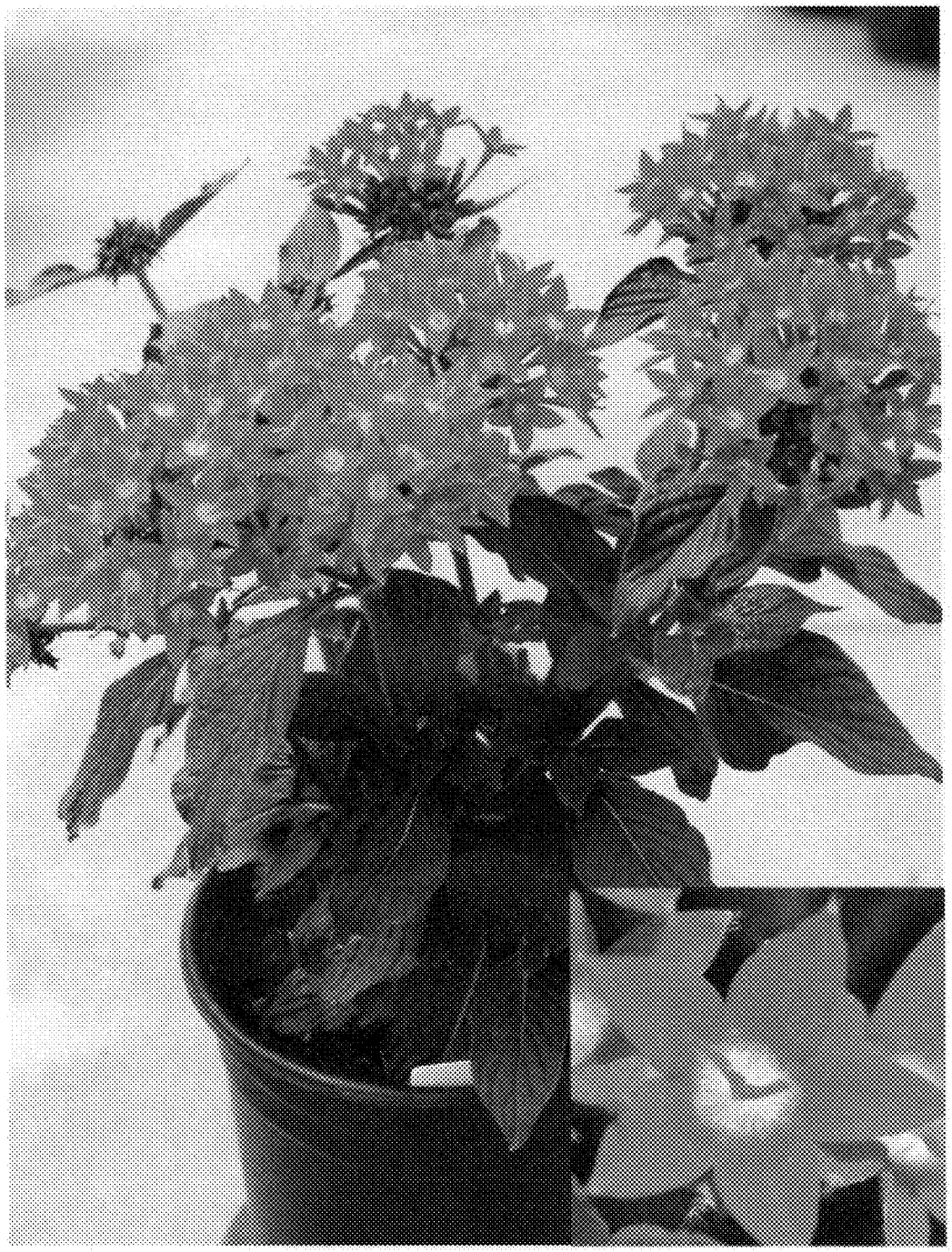

* * * * *